United States Patent [19]
Muller et al.

[11] Patent Number: 5,569,484
[45] Date of Patent: Oct. 29, 1996

[54] PROCESS FOR PRODUCING A FLAT ACTIVE SUBSTANCE ADMINISTRATION FORM

[75] Inventors: Walter Müller, Neuwied; Dieter Anhäuser, Melsbach, both of Germany

[73] Assignee: LTS Lohmann Therapie-Systeme GmbH & Co. KG, Neuwied, Germany

[21] Appl. No.: 397,167

[22] PCT Filed: May 19, 1995

[86] PCT No.: PCT/EP93/02168

§ 371 Date: May 19, 1995

§ 102(e) Date: May 19, 1995

[87] PCT Pub. No.: WO94/06419

PCT Pub. Date: Mar. 31, 1994

[30] Foreign Application Priority Data

Sep. 12, 1992 [DE] Germany .............. 42 30 589.6

[51] Int. Cl.⁶ .............. A01N 25/00; A61J 13/00
[52] U.S. Cl. .............. 427/2.14; 427/2.23; 424/448; 424/449
[58] Field of Search .............. 424/405, 448, 424/449; 427/2.14, 2.23

[56] References Cited

U.S. PATENT DOCUMENTS

| | | | |
|---|---|---|---|
| 4,796,381 | 1/1989 | Kauth et al. | 427/256 |
| 4,915,950 | 4/1990 | Miranda et al. | 424/448 |
| 5,110,599 | 5/1992 | Anhäuser et al. | 424/449 |

FOREIGN PATENT DOCUMENTS

| | | |
|---|---|---|
| 0 215 225 | 3/1987 | European Pat. Off. . |
| 0 303 025 | 2/1989 | European Pat. Off. . |
| 1 461 280 | 2/1969 | Germany . |
| 1 939 437 | 3/1977 | Germany . |
| 3 531 795 | 3/1987 | Germany . |
| 3 727 232 | 2/1989 | Germany . |

OTHER PUBLICATIONS

Korehoo KK, Patent Abstracts of Japan, vol. 016, No. 342 (C-0966) 24 Jul. 1992 JP A-04-100981, 2 Apr. 1992.

*Primary Examiner*—Thurman K. Page
*Assistant Examiner*—Kathryne E. Shelborne
*Attorney, Agent, or Firm*—Wenderoth, Lind & Ponack

[57] ABSTRACT

A process is provided for the production of a flat administration form with a dosable portion of drugs or of a flat-shaped device for the dosable release of volatile substances, such as aromatic substances, to the ambient air by using high-volatile or thermolabile dosing media in liquid or semisolid state as the ingredients of the administration form or of the device by means of printing processes. A free-flowing preparation of the ingredients is knife-coated in a measured amount into at least one volumetrically defined cavity of a flat printing block. A substrate to be charged with the ingredients or dosing media, respectively, is gradually led as web-shaped material under web tension over the cavity of the printing block and pressed into the filled cavity by means of a mechanical pressure device whereby the substrate takes up the ingredient from the printing block in a dosed amount.

15 Claims, 5 Drawing Sheets

PROCESS FOR PRODUCING A FLAT ACTIVE SUBSTANCE ADMINISTRATION FORM

A method of high-volatile or thermolabile substances in liquid form for the production of a. flat administration forms, in particular for the production of transdermal or dermal therapeutic systems, and b. flat-shaped devices releasing volatile substances to the ambient air

BACKGROUND OF THE INVENTION

The present invention relates to a process for the production of a flat administration form having a drug portion capable of being dosed or of a flat-shaped device for the dosable release of volatile substances, such as aromatic substances, to the ambient air by using high-volatile or thermolabile dosing media in liquid or semisolid state as the ingredients of the administration form or of the device by means of printing processes, wherein a flowable preparation of the ingredients is knife-coated in a measured amount into at least one volumetrically defined sink of a flat printing block. In the production of substantially flat-shaped administration forms or devices, this process is to permit the amount of liquid active substances, liquid active substance preparations, and/or liquid active substance/adjuvant mixtures to be dosed to the other components of the administration form or device in an accurate and superficially even manner.

Such flat-shaped administration forms may, for example, be transdermal therapeutic systems, transmucosal systems, dermal, i.e., only topically effective, systems, but also those to be administered orally, such as sublingual tablets or sublingual wafers. The process is of particular value in the production of transdermal or dermal systems of the matrix type and membrane systems with a fixed reservoir.

Since the function of such transdermal or dermal therapeutic systems and the materials required for their production are well known to the skilled artisan, it is only mentioned in a few words that the active substance(s) is/are present in the usually self-adhesive systems in an at least partially dissolved form; and after application of the system on the skin they diffuse from the system into the skin, developing a local or systemic effect.

The present invention will be illustrated in the following with reference to the accompanying drawings by comparison with the state of the art.

The most simple construction is that of known, single-layer matrix systems. According to FIG. 1 they may consist of an impermeable backing layer 3, a self-adhesive matrix layer 2, and a removable protective layer 1.

The matrix layers (and the same applies to reservoir layers of the above-mentioned membrane systems) are usually manufactured in such a manner that components of the matrix and active substances, dissolved in a solvent, are coated on a suitable sheet or film (removable protective layer 1), and that the solvents are removed in a drying process. This production method may cause considerable difficulties if ingredients are required that are either incompatible with the solvents or very temperature-sensitive; or if they have an excessively high vapor pressure at the drying temperature.

Examples of thermolabile active substances include, for example, vitamin $D_3$-derivatives; examples of active substances having an excessive volatility include the active substances nicotine or nitroglycerin, for example. Another important group of substances used for dermal or transdermal therapeutic systems are the so-called penetration enhancers. The function of these penetration enhancers is to facilitate the passage of active substances through the skin.

Examples of high-volatile penetration enhancers include, for example, terpenes (eucalyptol, camphor, etc.); esters (ethyl acetate, ethyl propionate, etc.); alcohols (ethanol, propanol, propanediol, etc.); or ketones (methyl hexyl ketone; methyl octyl ketone, etc.).

Incompatibilities between solvents and components must be expected whenever a chemical reaction may take place between them. For instance, alcohols are used for many adhesives; these may then react with active substances which have a free carboxyl group or an ester group in the form of an esterification or transesterification.

In order to avoid these difficulties, processes have been developed wherein a liquid preparation of the problematic substances is applied on a flat substrate at room temperature, and said substrate is then located between prefabricated layers of the administration form that is to be formed. The liquid preparation with all its diffusible components completely migrates into these layers within some hours or days. Such a substrate may consist, for example, of a paper film, a non-woven fabric, a textile fabric, or other absorbent materials. The most simple situation is given when a material (5) according to FIG. 2 which is impregnated with a liquid preparation is located between a laminate consisting of an impermeable backing layer (3) and a self-adhesive anchoring layer (6) and a second laminate consisting of a removable protective film (1) and another self-adhesive layer (4) contacting the skin.

Alternatively, the substrate to be impregnated may also be laminated on either of the self-adhesive layers 4 or 6, prior to application of the liquid preparation.

The finished systems (FIG. 3) are punched out of a large-area total laminate, for this reason it is advantageous—in case very expensive active substances or adjuvants, or active substances involving a great danger of misuse, e.g., narcotics, are used—to apply the liquid preparation in the form of patterns corresponding to the shape of the systems that are to be produced so that the resulting waste punchings are free from said substances.

U.S. Pat. No. 4,915,950 describes a method of producing such systems. Arbitrary dosing processes are generally summarized herein under the term printing process. The following are mentioned separately: gravure printing, extrusion coating, screen printing, spraying, and spread coating. However, none of the examples given herein exactly describe which special printing process was used for the respective production.

For this reason, it cannot be evaluated to what degree the employed production processes meet the demands to be made for drugs with respect to accuracy of dosage.

DE 35 31 795 A1 describes another example of a system wherein active substance-containing regions and active substance-free waste areas are applied on a carrier material and separated by punching subsequently.

It is said that an accurate dosage of the active substances can be achieved by means of exactly engraved or etched printing rolls or printing plates. The separation into active substance-free and active substance-containing zones is effected by means of printing methods which are not explained in greater detail-screen printing, flexographic printing, gravure printing, or noncontact printing processes, such as ink-jetting or spraying through nozzles and the like, are mentioned. However, there are no indications with respect to the way the known printing processes manage to keep to given accurate dosage quantities of active substances at defined concentrations per unit area. Apparently, this is not important because mothproof paper is concerned which releases an insecticidal aromatic substance to the ambient air over longer periods; in contrast to an administration form having skin contact, an exact concentration per unit area is not required.

OS 37 27 232 describes a special printing process, a so-called tampon printing process, for the active substance dosage in the production of transdermal or dermal systems.

Modern tampon printing processes have been known since 1968; a tampon printing unit is described in DE-OS 19 39 437, for example. Said printing technique is particularly suitable to print uneven surfaces because a deformable tampon transferring the printing medium adapts to the substrates to be printed.

In this process, the pattern to be printed is etched into a metal plate 10. The printing medium 12—referred to in the following description as dosing or metering medium—is transferred into the etched sink 14 (FIG. 4a), metered by means of knife coating (FIGS. 4b and c), subsequently taken up by the tampon 16 (FIGS. 4d and e), and transferred to the article 8 to be printed (FIG. 4f).

The disadvantage of this process is the fact that the transferred active substance quantities depend on a great variety of factors. Primarily, these are determined by the etched depth of the printing form; but also, for example, by the viscosity and cohesion of the metering medium, the adhesion of the metering medium to the plate material, and by the hardness and surface properties of the tampons that are used. For this reason, it may be difficult to coordinate these factors such that the desired measured weight is achieved and maintained over prolonged production periods. In particular if large areas are concerned and in case of a print image deviating from a circular geometry, it is very difficult to achieve an even area distribution of the metering medium. However, the even distribution of the dosing medium on the surface is of particular and decisive importance in the production of transdermal or dermal therapeutic systems.

In case of a dermal system, for instance, an irregular surface distribution of the active substance results in differently intensive actions over the complete application site; in case of a transdermal system the systemically available active substance amount may be determined by the active substance distribution. The concentration of the liquid or semisolid dosing medium in the administration form frequently influences the physical properties thereof. In case of dermal or transdermal systems—which for the most part are self-adhesive on their total contact surface to the skin—this primarily applies to the adhesive force and the cohesion. For instance, regions with an excessively high concentration may become too soft and therefore aggressively adherent, while regions with a low concentration possibly adhere poorly, consequently endangering the intense contact to the skin required for the function of the systems.

SUMMARY OF THE INVENTION

Accordingly, it was the object of the present invention to develop a new process for the accurate superficial dosing of liquid preparations, especially for the production of single-dose administration forms, in particular for the production of transdermal and dermal systems, which avoids the disadvantages of the processes described above.

According to the present invention, this object is achieved by a process characterized in that a substrate to be charged with the ingredients or dosing media, respectively, is gradually led as a web-shaped material under web tension over the cavity of the printing block and pressed into the filled cavity by means of a mechanical pressure device whereby the substrate takes up the ingredient from the printing block in measured amount.

DETAILED DESCRIPTION OF THE INVENTION

Figure 5A:
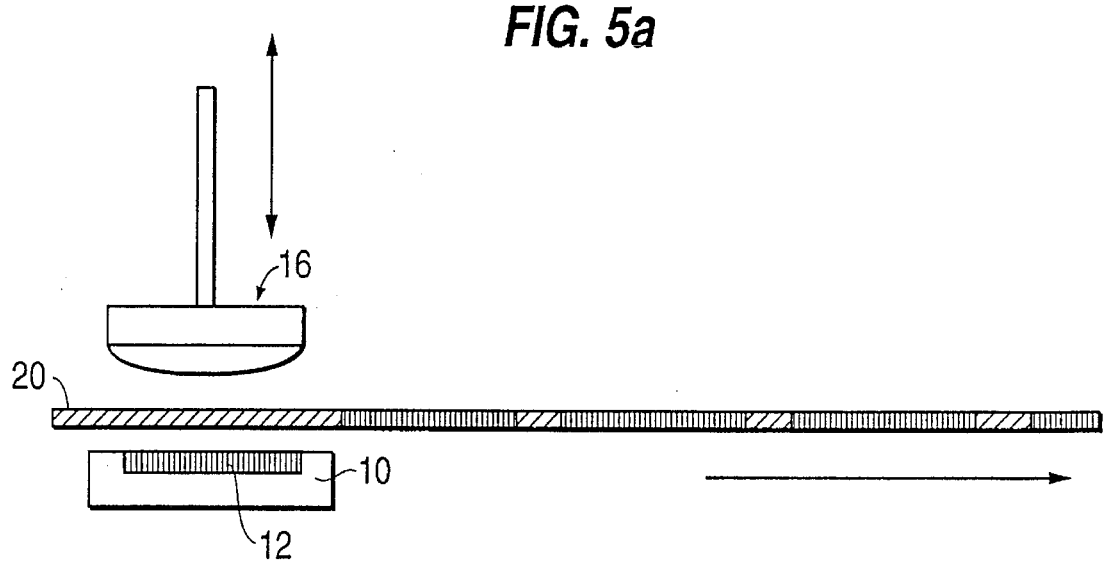
FIGS. 5a and 5b show a sequence of operations of the printing process according to the present invention.
Figure 5B:
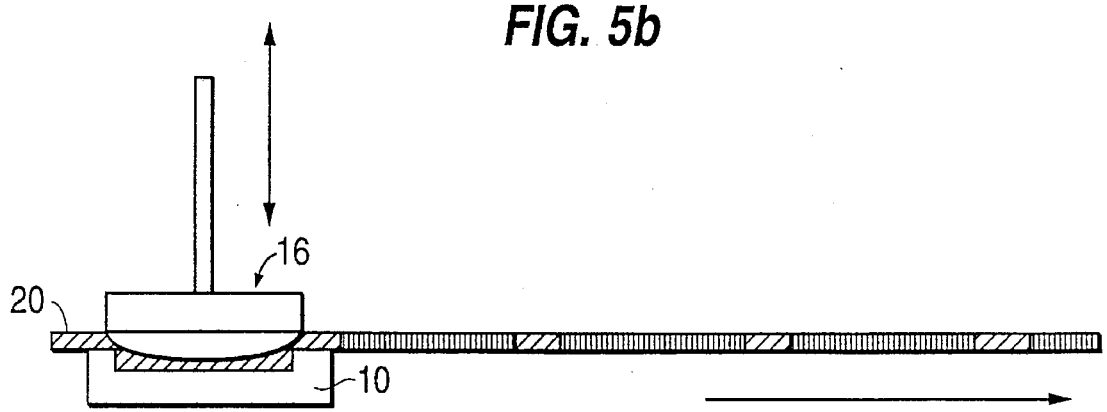
Figure 6:
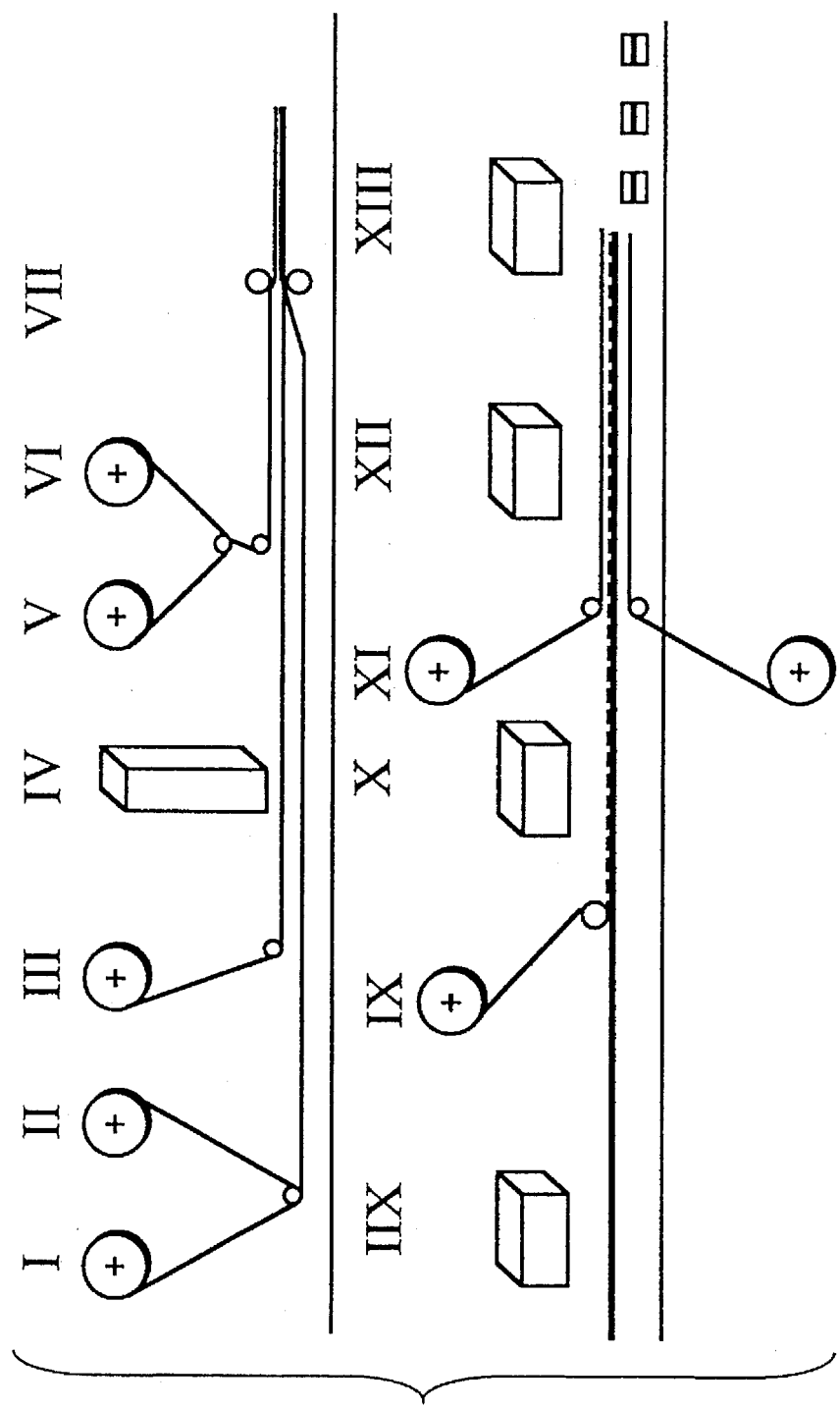
FIG. 6 shows a schematic representation of a continuous production of administration forms and devices in the form of a flowsheet.

The principle of the present invention is illustrated in FIGS. 5a–5b and in FIG. 6.

Figure 4A:
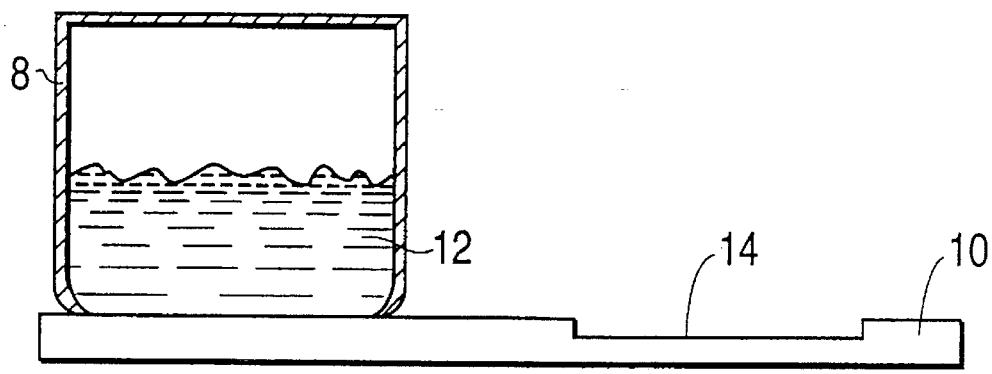
FIGS. 4a to 4f show in schematic representation a sequence of operational steps in a known printing process.
Figure 4B:
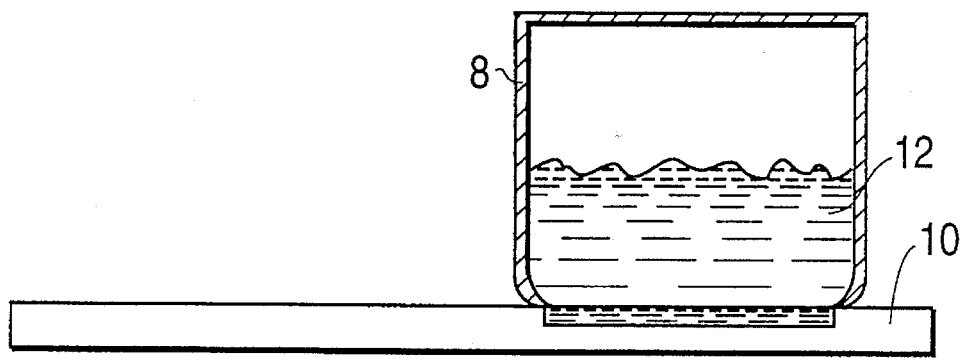
Figure 4C:
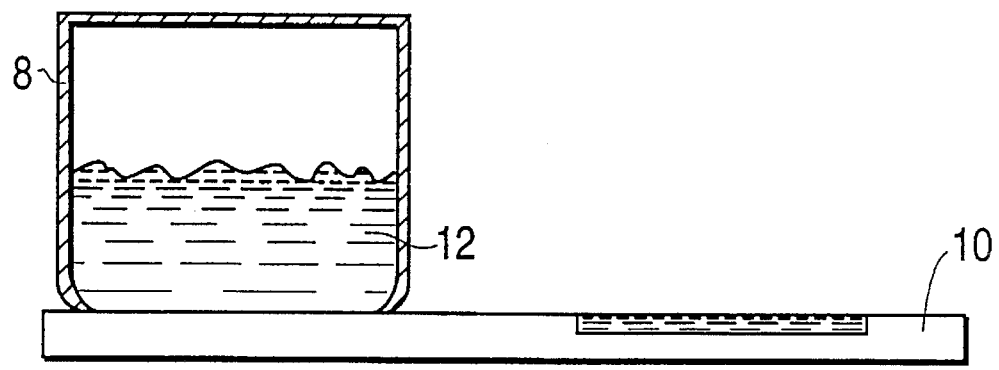

At first the cavity 14 is filled with metering medium 12 as shown in FIGS. 4a–4c and spread by means of a knife coating procedure. In contrast to the described prior art, the substrate to be printed is then led over the cavity in the form of a web-like material 20 (FIG. 5a)

Figure 4D:
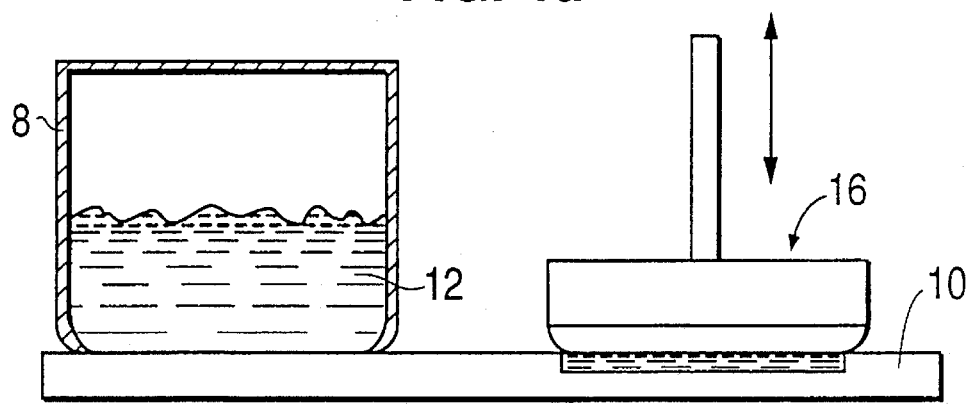
Figure 4E:
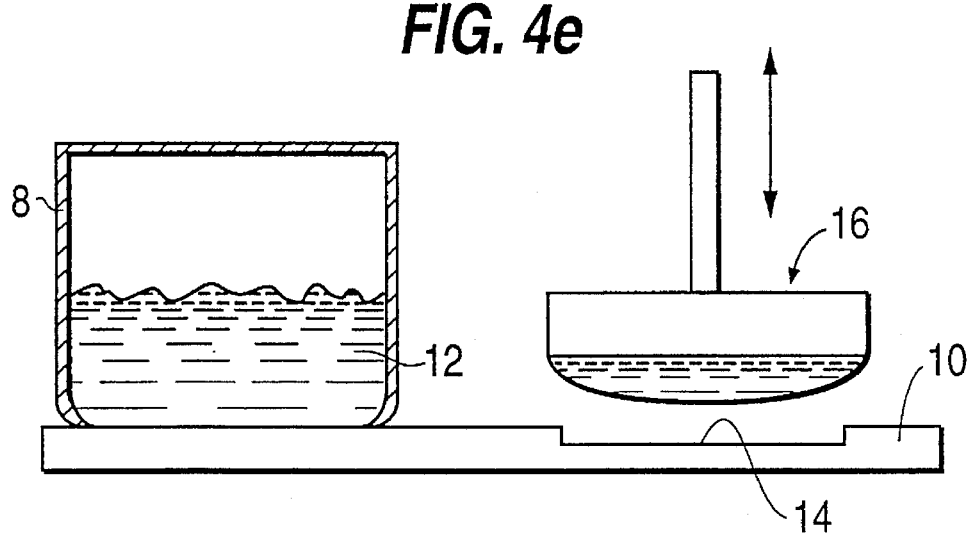
Figure 4F:
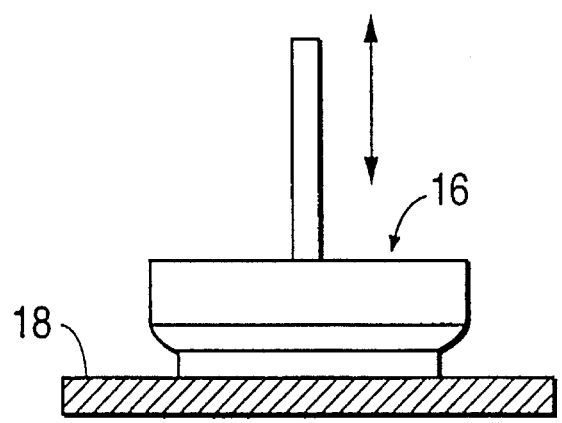

This is possible if the reservoir 8 for the dosing medium is fixed in its position and if the plate 10 with the sink (cavity) 14 is the moving part in the filling process (i.e. the plate 10 reciprocates between a first position as shown in FIGS. 4c and 4d, and a second (cavity filling) position as shown in FIG. 4b).

By means of a mechanical device the web-shaped substrate tape 20 is pressed cyclically (i.e. intermittently) into the filled sink 14 and takes up the dosing medium (FIG. 5b). The web tension causes the tape 20 to come out of the cavity 14 again.

A lot of possibilities are suitable for the mechanical device which presses the material into the filled sink 14.

For instance, this may be a soft tampon performing up and down movements. Another possibility consists in placing an elastic membrane—for example like in a drum—as a closure onto a hollow body; then overpressure is applied to this hollow body in the cycle rate of the production. In this connection, the vaulting membrane presses the substrate into the cavity.

Since, strictly speaking, this process is a very exact volumetric feeding in principle and the transfer by means of a tampon is omitted, a considerable accuracy and reliability is gained, as compared with the known processes, e.g., according to DE-OS 37 27 232. In contrast to a tampon, the substrate may have absorbing properties, consequently the maximum quantity of dosing medium that can be transferred is considerably larger. It is easy to proportion problematic components according to the present invention, if these ingredients themselves are liquid at room temperature. In other cases, solvents can be found which may remain in the finished system without detriment to the user; or it is possible to melt the dosing medium.

Since especially penetration enhancers are liquids in many cases, it is frequently possible to dissolve the active substance in these penetration enhancers and to dose them together.

Figure 3:
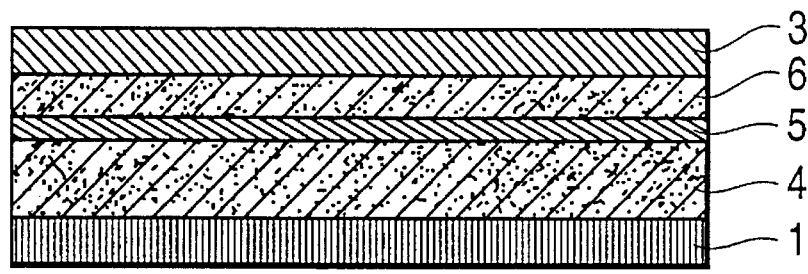
FIG. 3 shows a sectional view of the finished laminated layers of the administration form according to FIG. 2.

For this process the metering media must have a certain minimum viscosity. In this connection, viscosity-increasing additives, e.g., aerosils or polymers, may help; they may be either of a natural origin, e.g., gelatin, starch derivatives, or of a synthetic origin, e.g., polyacrylic acid derivatives. A system of the construction exemplified in FIG. 3 is produced according to the present invention in correspondence with the production scheme shown in FIG. 6.

In position I of the scheme, there is a supply roll of the self-adhesive matrix layer 4 which is positioned on the protective film; after application this matrix layer is in contact with the skin, and it is covered by a removable film. The film is removed and wound on a roll in position II. In position III, there is a supply roll for the substrate 5.

Figure 1:
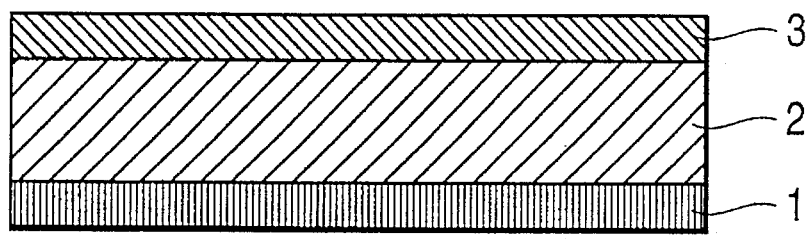
FIG. 1 shows a known administration form having a backing layer, a self-adhesive matrix, and a removable protective film.
Figure 2:
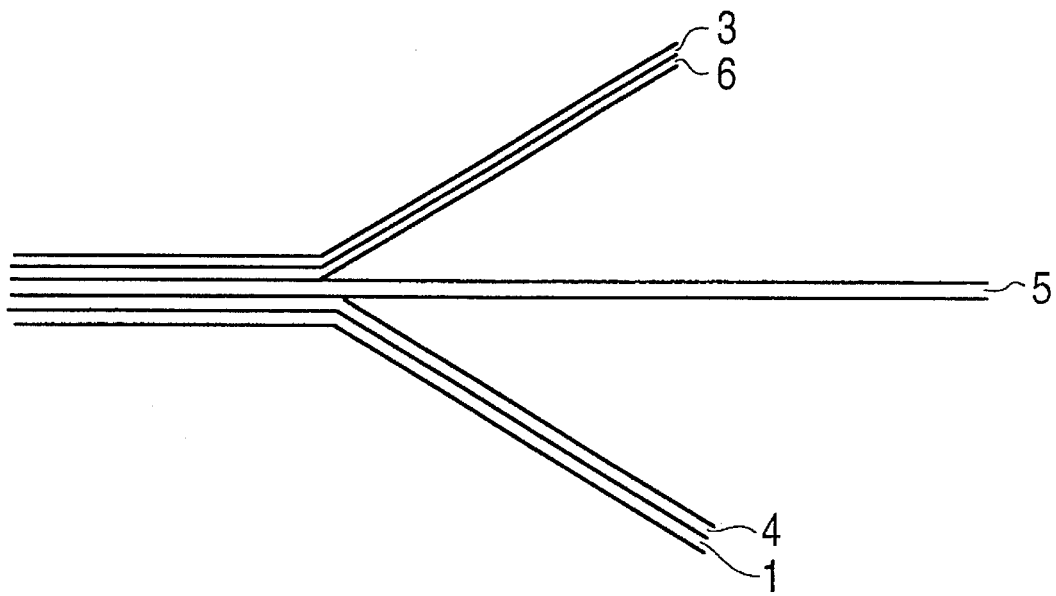
FIG. 2 represents an administration form comprising a backing layer, a first and second matrix layer with a substrate layer positioned between them, and a removable protective film; in laminated state.

Position IV represents the dosing station for the liquid preparation at which the substrate (5) is pressed cyclically (i.e. intermittently) into the cavity of a printing block filled with dosing medium. In position VI, there is a supply roll for the self-adhesive matrix layer 6 which is positioned between the backing layer and a removable film. The removable film is wound up on a take-up roller in position V. The printed substrate is laminated between the two matrix layers in position VII (cf. FIG. 2). The individual patches and transdermal or dermal systems, respectively, are obtained by subsequent punching procedures. That is, the active substance-containing administration form is separated from surrounding active substance-free waste portions by means of a subsequent punching procedure. The active substance-free waste is then wound on a waste roll. The administration forms or devices are separated by means of a cross cutter and in a packing station are covered by strips of packing material first, then sealed on all sides by means of hot sealing, and finally separated into individual, tightly sealed units by means of cross-cutting.

The metered ingredients now diffuse into the matrix layers according to Fick's laws of diffusion. Usually, this process is completed after only a few days.

According to a modification of the process, the backing layer with matrix layer 6 is laminated with the substrate 5 before the dosing station; accordingly only the matrix layer 4 positioned on the protective film is laminated in position VII.

Other modifications of the process are possible and lie within the scope of the present invention.

The process provides a very even distribution of the metered ingredients within the systems. The accuracy and reproducibility that can be achieved are of such a quality that administration forms produced by this process meet the pharmacopeial requirements with respect to drugs.

In this connection, patches whose maximum dimension in one direction may amount to up to 15 cm can be manufactured by the process according to the present invention. The size of a square patch may therefore amount to up to 225 $cm^2$.

In case of such large formats, the recess to be filled is advantageously divided into smaller individual areas which are separated by narrow gates. If necessary, these gates may be very narrow, i.e., about 0.2 mm in width; thus their portion of the total area is very small.

If the dosed components are highly volatile substances, the individual patches are advantageously directly packaged on-line. Four-edge sealed bags are the preferred packaging material. Four-edge sealed bags the innermost layer of which consists of polymers based on acrylonitrile have proved to be suitable in nearly every situation; in this connection the polymer Barex®(BP Chemicals) is to be mentioned as particularly suitable.

When an on-line packing is used, it is possible to incorporate problematic components according to the present invention into single-layer matrix systems. In this connection, the backing layer of the finished patch must, however, be permeable to the dosing medium, and the dosed substances must have a certain volatility. Materials for a permeable backing layer are, for example, textile materials, sheets of polyurethane or ethylene-vinyl-acetate-copolymers. With these systems the dosing medium is metered on the backing layer or supporting material of the already punched out patch, and the patches are then immediately packed in the primary package.

Another possibility of producing such single-layer systems is to meter the problematic ingredients onto a separate absorbent flat-shaped material and pack this together with the patch, ideally in contact with the permeable backing layer thereof. In the impermeable primary package (four-edge sealed bag) the dosed medium then diffuses into the self-adhesive matrix of the patch.

Systems having a permeable backing layer release their volatile ingredients to the ambient air as soon as they are removed from the primary packaging material. Whereas this may be disadvantageous for an administration form, this effect can advantageously be used for the production of devices which release aromatic principles, insecticides, or insect repellents. If such devices are to be stuck on the skin, the absorption of these agents through the skin can be prevented by integrating an impermeable film into the device.

Apart from that, the production process of such devices is identical with the production of dermal or transdermal systems described in great detail hereinbefore—at least as far as the relevant production steps according to the present invention are concerned.

Example:

Production of a transdermal therapeutic system with eucalyptol as penetration enhancer can be accomplished according to the construction of FIG. 3 and the production scheme of FIG. 6.

The self-adhesive matrix layer 1 has a weight per unit area of 25 $g/m^2$ and is protected by an adhesive (siliconized) polyethylene film used as intermediate cover.

The backing layer consists of a polyester film of 12 μm thickness.

Matrix layer 2 which is also self-adhesive has a mass per unit area of 100 $g/m^2$ and is positioned on an adhesive polyester film having a thickness of 100 μm. It is also protected by an adhesive polyethylene film as intermediate cover.

Both matrix layers already comprise the active substance so that only the penetration enhancer eucalyptol has to be proportioned. Eucalyptol is a highly volatile and thin substance. The viscosity is increased to about 3 Pas.s by the addition of 3% ethylcellulose and it can therefore be used according to the present invention.

The substrate to be printed consists of a long-fiber paper and has a basis weight of 30 g/m².

The patch has a size of 32 cm² (4×8 cm) and is rectangular with rounded edges.

The sink in the dosing plate has a depth of 140 μm and its dimensions are each 1 mm larger than the patch.

As is mentioned in the description, the polyethylene protective film is removed from both matrix layers, the long-fiber paper is printed and laminated between both matrix layers. Subsequently, the individual patch is punched out of the web-like laminate and packed on-line.

The metered amount of eucalyptol amounted to 140 μg/patch or 4.3 mg/cm², and the standard deviation (n=10) amounted to about 2.6%.

We claim:

1. A process for the production of a flat administration form having a drug portion capable of being dosed or of a flat-shaped device for the dosable release of volatile substances to the ambient air by using a high-volatile or thermolabile dosing medium in liquid or semisolid state as ingredients of the administration form or of the flat-shaped device, said process comprising:

providing a reservoir containing a flowable preparation of the dosing medium;

providing a reciprocable printing plate having a dose-receiving cavity therein;

knife-coating a measured amount of the dosing medium from the reservoir into the dose-receiving cavity by maintaining the reservoir in a fixed position and reciprocating the printing plate between a first position in which the reservoir is non-aligned with the dose-receiving cavity and a second position in which the reservoir is aligned with the dose-receiving cavity to fill the dose-receiving cavity with the measured amount of the dosing medium;

guiding a tensioned web-shaped material along a travel path to a dosing station, the dose-receiving cavity of the printing plate being aligned under the web-shaped material at the dosing station when the printing plate is in said first position; and intermittently pressing a mechanical device against the web-shaped material to press the web-shaped material into the filled dose-receiving cavity when the filled dose-receiving cavity of the printing plate is aligned under the web-shaped material, whereby the web-shaped material takes up the dosing medium from the dose-receiving cavity of the printing block.

2. The process according to claim 1, further comprising adding the web-shaped material to the administration form as a component thereof.

3. The process according to claim 1, further comprising contacting the web-shaped material printed with dosing medium against the administration form or the device in such a manner that the dosing medium is transferred from the web-shaped material to the administration form or the device by diffusion.

4. The process according to claim 1, wherein the administration form is a dermally applicable system.

5. The process according to claim 4, wherein the dermally applicable system is a transdermal therapeutic system.

6. The process according to claim 4, wherein the dermally applicable system is a topically effective therapeutic system.

7. The process according to claim 1, wherein the administration form is an orally applicable system.

8. The process according to claim 1, wherein the dosing medium comprises an active substance.

9. The process according to claim 8, wherein the active substance is dissolved or suspended in at least one penetration enhancer.

10. The process according to claim 1, wherein the dosing medium comprises adjuvants and is active substance-free.

11. The process according to claim 1, wherein the dosing medium comprises a penetration enhancer.

12. The process according to claim 1, wherein the dosing medium comprises an aromatic substance.

13. The process according to claim 1, wherein the dosing medium comprises an insecticide or insect repellent.

14. The process according to claim 1, wherein prior to the steps of guiding the tensioned web-shaped material along the travel path and intermittently pressing the mechanical device against the web-shaped material, performing the steps of removing an adhesive intermediate cover from a self-adhesive first matrix layer which is positioned on a protective film and is adapted for contact with the skin upon application of the administration form, and winding the intermediate cover on a roll;

in the step of guiding the tensioned web-shaped material along the travel path, the web-shaped material is unwound from a supply roll and gradually led along the travel path to the dosing station;

after the step of intermittently pressing the mechanical device against the web-shaped material:
  removing a protective film from a self-adhesive second matrix layer which is placed on an adhesive protective film;
  winding the self-adhesive second matrix layer on a roll;
  laminating the web-shaped material, which has been printed with the dosing medium, between the self-adhesive first and second matrix layers; and
  separating dosing medium-containing portions of the web-shaped material from waste portions thereof which do not contain dosing medium by performing a punching procedure.

15. The process according to claim 14, further comprising after the step of separating the dosing medium-containing portions of the web-shaped material:

winding the waste portions of the web-shaped material onto a waste roll;

separating the dosing medium-containing portions of the web-shaped material by means of a cross cutter;

in a packing station, covering the dosing medium-containing portions of the web-shaped material with strips of packing material, and sealing the dosing medium-containing portions of the web-shaped material on all sides by performing hot sealing; and separating the sealed dosing medium-containing portions of the web-shaped material into individual, sealed units by performing cross-cutting.

* * * * *

UNITED STATES PATENT AND TRADEMARK OFFICE
CERTIFICATE OF CORRECTION

PATENT NO. : 5,569,484
DATED : October 29, 1996
INVENTOR(S) : Walter MÜLLER et al.

It is certified that error appears in the above-indentified patent and that said Letters Patent is hereby corrected as shown below:

On the cover page, item [22] should read:

--[22] PCT Filed: August 16, 1993--

Signed and Sealed this

Fourth Day of March, 1997

Attest:

BRUCE LEHMAN

Attesting Officer

Commissioner of Patents and Trademarks